United States Patent [19]

Thomson et al.

[11] 3,943,072

[45] Mar. 9, 1976

[54] SEPARATION OF MOLECULES

[75] Inventors: Alan Russell Thomson, Abingdon; Brynley John Miles, Faringdon, both of England

[73] Assignee: United Kingdom Atomic Energy Authority, London, England

[22] Filed: Mar. 28, 1974

[21] Appl. No.: 455,948

Related U.S. Application Data

[63] Continuation of Ser. No. 312,287, Dec. 5, 1972, abandoned.

[30] Foreign Application Priority Data

Dec. 15, 1971 United Kingdom............... 58374/71

[52] U.S. Cl.............. 252/455 R; 252/437; 252/440; 252/461; 252/463
[51] Int. Cl.² B01J 21/16; B01J 27/18; B01J 27/02; B01J 21/04
[58] Field of Search........ 252/437, 440, 455 R, 461, 252/463, 477 R

[56] References Cited
UNITED STATES PATENTS

| | | | |
|---|---|---|---|
| 2,593,720 | 4/1952 | Bielawski | 252/435 X |
| 2,697,066 | 12/1954 | Sieg | 252/465 X |
| 2,755,236 | 7/1956 | Robinson | 252/474 X |
| 2,840,530 | 6/1958 | Milliken et al. | 252/455 R |
| 3,417,028 | 12/1968 | Montgomery et al. | 252/451 X |

OTHER PUBLICATIONS

Kirk–Othmer, *Encyclopedia of Chemical Technology*, p. 451, 2nd Edition, Vol. I.

*Primary Examiner*—Patrick P. Garvin
*Attorney, Agent, or Firm*—Larson, Taylor and Hinds

[57] ABSTRACT

Porous material particularly suitable for selective sorption and retention of macromolecules are manufactured by mixing a finely divided inorganic material with a fugitive additive, forming into discrete particles and heat treating to remove fugitive additive. The fugitive additive is a solid which is preferably mixed with the inorganic material after dissolving the additive in a solvent which is not a solvent for the inorganic material.

11 Claims, No Drawings

SEPARATION OF MOLECULES

This is a continuation of application Ser. No. 312,287, filed Dec. 5, 1972, now abandoned.

The present invention relates to the separation of molecules from fluid substances containing such molecules and finds one application in the separation of organic molecules known as macromolecules.

It is often necessary to separate molecules of a particular substance from a mixture of substances, and in fields in which one encounters macromolecules (i.e. molecules of high molecular weight, for example protein molecules) it is known to carry out separation and fractionation of molecules by use of chromatographic techniques. In such techniques predetermined molecules are sorbed onto a material which is capable of selectively abstracting said molecules from the mixture and later the material is treated with eluting agents in order to effect elution of the sorbed molecules. The term "sorption" is used in this specification to indicate the retention of the molecules by the material and embraces, for example, absorption and adsorption (which includes physisorption and chemisorption).

Organic and inorganic materials have been used for the separation of macromolecules, but these materials suffer from certain disadvantages. Organic materials, such as natural polymers (e.g. cellulose), modified natural polymers (e.g. ion-exchange celluloses and cross-linked dextrans), and synthetic polymers (e.g. ion-exchange resins and cross-linked polyacrylamides) have been used in macromolecular separations. However, in order to allow entry of large molecules the pores of the material must be large and, as a result of this open structure, the material tends to be readily compressible and undergoes swelling and shrinking with changes of pH and ionic strength of the media with which the materials are contacted. In addition, the natural polymers and the modified natural polymers are susceptible to microbiological attack and have limited stability to acids and alkalis. In addition, some organic materials also tend to be costly. Further it has been found in practice that scale up of operations with these materials is difficult because of their poor physical characteristics for column operation (i.e. as a bed packed in a column apparatus).

These materials have been used for batch and column fractionation, deionization, and to some extent for concentrating macromolecules from dilute solution.

A number of inorganic materials have also been used for separating macromolecules; such materials include calcium phosphate, both as crystals (hydroxylapatite) and in the form of gels, barium sulphate, porous silica, porous glass, aluminium oxide, hydroxide and phosphate as powder and in gel form, magnesium pyrophosphate as a gel and zinc oxide powder. Of these only calcium phosphate, barium sulphate and alumina gel are used to any great extent.

Hydroxylapatite has been used in the form of crystals but practical difficulties arise since small particle sizes are required to give a large sorptive area and since the crystals tend to be fragile and break up to give "fines". It is found that columns of this material tend to block due to the presence of fine material and the column is seldom re-used; the material is little used on other than a laboratory scale.

Barium sulphate has been used for the adsorption of certain clotting factors from blood plasma, but the small size of the crystals required to give a high adsorptive capacity means that the material is difficult to handle and in addition it is found that the material is unsuitable for use in columns. The gels mentioned above are difficult to prepare reproducibly and cannot be used in columns except when mixed with a filler (e.g. cellulose, or kieselguhr) when undesirable, non-specific adsorption effects often occur. Porous silica and glass are costly and are used for molecular sieving; considerable effort has been devoted to reducing adsorption effects in these materials since these effects tend to be irreversible and/or lead to loss of biological activity.

Ideally, materials for separating macromolecules should be stable to pressure, temperature and chemical reagents (including aqueous solutions) and should cause minimal damage to the macromolecules with which they are contacted.

To summarise, materials previously used in the separation of macromolecules from substances containing such macromolecules have suffered from practical disadvantages arising out of their physical properties.

According to one aspect of the present invention, a method for producing an inorganic material having interconnected porosity throughout the material for the selective retention of predetermined molecules from a fluid substance containing the molecules includes the steps of mixing a finely divided, substantially insoluble, sorptive, inorganic material, capable of sorbing the molecules, with a solid fugitive additive to form a mixture, including in the mixture a solvent to dissolve fugitive additive in the solvent, the inorganic material being substantially insoluble in the solvent, forming discrete particles from the mixture, and heating the particles to remove solvent and fugitive additive to produce discrete particles of the inorganic material having an interconnected pore structure throughout the discrete particles providing an extended surface area, the pore size being such as will allow the predetermined molecules in the fluid substance to permeate the inorganic particles and be sorbed, the inorganic material being substantially unaffected by the heating utilized to effect removal of solvent and fugitive additive.

In a preferred embodiment of the invention, the substantially insoluble, sorptive, inorganic material is also mixed with a binding agent in addition to a fugitive additive.

"Sorptive" as used herein with reference to a material from which particles may be formed means that the material either is of its nature sorptive, or may be treated to make it sorptive.

The term "substantially insoluble" as used herein means that the material is substantially insoluble in the substance containing the molecules and in eluting agents used to recover the molecules from the material.

According to another aspect of the present invention, a material for the selective retention of predetermined molecules from a fluid substance containing said molecules comprises discrete particles formed from substantially insoluble, sorptive, inorganic material capable of sorbing the molecules, said particles having a pore structure such as will allow the predetermined molecules to permeate the particles to be sorbed.

Preferably the particles according to the present invention are substantially spherical in shape and are of a size convenient for use in chromatographic operations (typically 50–600 $\mu$ diameter) in which case they can be easily handled, and tend not to produce "fines", thus, in one application, they present less difficulty from the point of view of blocking when used in a column apparatus. (For some applications a size of 2 $\mu$ could be useful and in others a size of 1 mm may be preferred). At the same time the particles have a useful sorptive capacity due to their porous structure (interconnected porosity). The particles have good column properties, tend to be mechanically strong and tend to settle rapidly to form well-packed column beds which can be pumped at high flow rates. The particles can also be used in batchwise and in fluidised bed processes.

It is to be understood that in materials according to the immediately preceding aspect of the invention it is substantially the sorptive properties of the material which is being utilised to select the molecules. Furthermore it is believed that in certain instances separation can be achieved by further specific interactions between the material and the sorbed molecules. This may be achieved, for example by appropriate selection of the sorbent materials or by additions thereto to promote the specific interactions, e.g. metal-macromolecule interactions.

It is also possible to control the formation of the pore structure of the particles such that molecules being larger than a predetermined size are excluded from entering the particles.

Thus, according to a further aspect of the present invention a material for the selective retention of predetermined molecules from a fluid substance containing said molecules comprises discrete particles formed from substantially insoluble sorptive inorganic material capable of sorbing the molecules, said particles having a pore structure such as will act in the manner of a molecular sieve so that molecules being larger than a predetermined size are prevented from permeating the particles to be sorbed whilst molecules being smaller than the predetermined size may permeate the particles to be sorbed.

It is to be understood that in materials according to the immediately preceding aspect of the invention both the sorptive and molecular sieve properties of the material are being utilised to give enhanced resolution to the molecular separation.

The pore structure of the particles and thus the size of molecules excluded or allowed to permeate can be varied by incorporating appropriate fugitive additives at the manufacturing stage.

When the porous particles are used in the separation of molecules the molecules sorbed by the porous particles may be subsequently recovered therefrom by contacting the porous particles with an eluting agent. In the case where several species of molecules are sorbed from the fluid substance, by eluting with different eluting agents, or by otherwise altering eluting conditions, the sorbed species may be fractionated.

It is to be understood that it is possible to arrange for the material to sorb unwanted species of molecules from a mixture of wanted and unwanted species, in which case the wanted species will pass through the material and thus be recovered from the mixture.

A range of materials have been prepared in accordance with the present invention. Particles of substantially spherical shape have been prepared in the 50–600 $\mu$ size range from titanium dioxide ($TiO_2$), aluminium oxide ($Al_2O_3$), calcium phosphate, barium sulphate ($BaSO_4$) zirconium oxide and calcium sulphate. In addition particles have been formed from celite, a natural earth.

Pore sizes varied and between 80% and 87% of the pores were between 1000 A and 10,000 A (determined by mercury porosimetry, a standard technique). It is believed that pore sizes in the range 50 A and upwards should be suitable but it is to be noted that pore shape is important and the mercury technique yields only pore entrance diameters.

Unexpectedly, the pore size required for successful sorbtion of a molecule, is much greater than the size of the molecule to be sorbed. For example, albumin (150 A $\times$ 38 A) was not sorbed by a porous structure with about 80% of the pore between 1,000 and 4,300 A, but was sorbed by a porous structure with 60% of the pore between 2,700 and 10,000 A.

The fugitive additives used to generate porosity included ammonium carbonate, haemoglobin and polyvinyl alcohol (PVA), which led to products with consistent molecular exclusion limits. Other fugitive additives may be used to generate porosity, for example dextran, urea, bovine serum albumin and ovalbumin. In all the examples including $TiO_2$, calcium phosphate and $Al_2O_3$, the use of ammonium carbonate as fugitive additive resulted in materials which excluded lower molecular weight proteins than materials with haemoglobin as fugitive additive. Also, low molecular weight PVA yielded materials with lower molecular exclusion limits than high molecular weight PVA.

Temperatures which have been used in the production of materials are, for $TiO_2$ 900° C, for $Al_2O_3$ 600°–1200° C, for $BaSO_4$ 1200°–1400° C, and for calcium phosphate 1100° C. All materials were heated in air or $O_2$ and at atmospheric pressure. However, an inert atmosphere or a vacuum may be used.

To investigate the influence of heat treating conditions on the particle product, samples of "green" hydroxylapatite spheres were treated at elevated temperatures for different times and at different temperatures. The sorptive capacities of the treated spheres were then tested with haemoglobin as a "molecular proble".

A treatment temperature of 800° C for 1 hour gave material with the highest sorptive capacity, the capacity decreasing moderately with increases in temperature and treatment time.

Below 700° C, the material had a grey appearance, which incidated the presence of unremoved carbon.

In another investigation, scanning electron microscope studies showed that the particles produced by the orbital spherodisation route (see hereinafter) had surface porosity and particles that were sectioned showed that porosity extended throughout the particle.

There was reasonable agreement between the pore size distribution and that measured by B.E.T. and mercury porosimetry techniques.

The invention is further illustrated by the following specific examples which relate to the preparation of materials of the present invention.

EXAMPLE 1

Fine particle $TiO_2$ (<10$\mu$) was first prepared by filtering a suspension of $TiO_2$ in water. The basic orbital spheroidisation procedure was as described in British Pat. Specification Nos. 992,237 and 1,033,143 but modified as will be apparent from the following discussion. 500 g of the $TiO_2$ were mixed with a saturated solution containing 100 g ammonium carbonate and with 25 g of glycerol in 100 ml of water to make a slurry. This was allowed to dry slowly and was then passed through a 50 μ nylon sieve.

A similar quantity of $TiO_2$ was mixed with 100 g ammonium carbonate, but only 12.5% of glycerol. This was treated similarly.

The mixture with higher glycerol content was first spheroidised, by orbital spheroidisation, to the "caviar" stage, but as interest was in smaller particle sizes, these were only visible microscopically. When this occurred smaller quantities of the second mixture were gradually added, to yield green spheres of particle size 50μ – 500μ. These were sieved giving various cuts of different size range.

These separated green spheres were then heated at 900° C in air for 2 hours and yielded reasonably hard porous spheres which liberated only traces of free oxide on agitation in water and when used in columns, no fine material was detectable in the eluates either visibly or by UV absorption. They were stable to treatment with citrate, phosphate and pyrophosphate buffers, to 0.1M NaOH and 1N HCl. This material excluded all but the smallest proteins when tested.

EXAMPLE 2

500 g $TiO_2$ were ball milled with 40 g of haemoglobin (scale) for 2 hours. 120 g of this mixture was mixed with a solution containing 6 g glycerol in 60 ml water. Because of the larger crystallite size of the $TiO_2$, this produced smooth aggregates on spheroidisation after drying and passing through a 50 μ sieve. The green particles which were mainly 200–300 μ in size, were heated at 900° C for 2 hours in air and yielded aggregates with the same physical properties as Example 1, with the exception that the spectrum of sorbance of proteins was completely different. This material sorbed most of the proteins tested.

EXAMPLE 3

1 kg $TiO_2$ was slurried with 200 g PVA (Mol Wt 125,000) in 2 liters $H_2O$. On drying, this yielded a very hard resilient solid which was milled (ground) to give aggregates and produced 500 g of particles (100μ – 500μ). These were heated at 900° C for 1 hour in air. This material appeared to present an open structure to most proteins tested and had a capacity similar to Example 2.

EXAMPLE 4

200 g of calcium phosphate ($Ca_3(PO_4)_2$) were slurried with 30 g ammonium carbonate and 10 g glycerol dissolved in 165 ml water. A similar slurry containing only 5 g glycerol was also prepared.

The first slurry was spheroidised, after drying and passing through a 50 μ sieve, to the "caviar" stage and small quantities of the second mix were added subsequently. This produced green spheres of between 1000μ – 250μ, which were heated at 1100° C for 1 hour, in air. This material presented an open structure to most proteins but there was also frontal elution. It was stable to phosphate buffers and to 0.1M NaOH (but not to pyrophosphate); X-ray diffraction patterns showed this material to be mainly hydroxylapatite.

EXAMPLE 5

200 g $Ca_3(PO_4)_2$) were slurried with 40 g haemoglobin and 20 g glycerol in 100 ml $H_2O$, the mixture was dried and was passed through 200 μ sieve. 200μ – 150μ particles were collected and heated at 1100° C for 1 hour. This gave an open structured material which behaved substantially similarly to commercially available hydroxylapatite. (Bio-rad, Registered Trade Mark).

EXAMPLE 6

200 g of barium sulphate ($BaSO_4$) (Barium Meal grade B.P.) were slurried with 20 g ammonium carbonate and 10 g glycerol dissolved previously in 150 ml $H_2O$. A similar mix was prepared containing only 5 g glycerol. Both mixes were allowed to dry and were then sieved through a 50 μ mesh. The first mixture was then spheroidised to the "caviar" stage and spheres built up with the gradual addition of the second mix. Good spheres were formed in the range 200μ – 500μ and these were heated at 1300° C for 1 hour to yield spheres which were stable to buffers and 0.1M NaOH.

EXAMPLE 7

600 g of aluminium oxide ($Al_2O_3$) were slurried with 120 g ammonium carbonate and 60 g glycerol in 60 ml water and allowed to dry. This mixture was passed through a 50 μ sieve and spheroidisation was performed. It yielded a quantity of smooth aggregates in the range 100μ – 200μ, which were heated at 1200° C for 2 hours. The material was stable to phosphate and pyrophosphate buffers and to 0.1M sodium hydroxide. An ammonium sulphate fraction from horse muscle extract chromatographed with a stepwise buffer elution programme on columns of this material yielded a number of well separated peaks.

EXAMPLE 8

125 g of haemoglobin and 100 g of glycerol were dissolved in 500 ml of water. The solution was then added with continuous mixing to 500 g of celite, a natural earth. (The celite used was "celite 545" available from Koch Light Laboratories).

The resulting mixture was then dried overnight in an oven at 70° C and subsequently passed through a 200 μ mesh sieve and spheroised to give a spheroidal material.

Spheroids of 200 μ were separated from the bulk material and were heated at 900° C for 1 hour. Scanning electron micrography showed the spheroids to have interconnected pores and clearly showed them to be composed of the very characteristic perforated diatomaceous earth platelets.

EXAMPLE 9

A slurry was made of 1000 g $Ca_3(PO_4)_2$ and 200 g haemoglobin (which had previously been dissolved in 750 ml of water). The volume of the slurry was adjusted to 3 liters.

The slurry was fed into a spray-drying apparatus wherein spheres were formed. The spheres were separated according to size with a fluid bed compressed air system. The larger size fraction of material was heated for 1 hour at 900° C.

The uniform spheres were found to have a comparable protein sorption capacity to material produced using orbital spheroidisation as in preceding examples.

Mercury porosimetry data for (a) $TiO_2$ particles produced using ammonium carbonate as the fugitive additive and for (b) $TiO_2$ particles produced using haemoglobin as the fugitive additive reveals that for (a) approximately 80% of the pores had a size in the range 0.45 – 0.1 μ, and that for (b) approximately 80% of the pores had a size in the range 2.4 – 0.1 μ.

It will be apparent from the foregoing examples that the solvent can be utilized in various ways. For example, the solvent can be added after mixing the inorganic material and fugitive additive in a dry state (as in Example 2). Another and preferred technique is to dissolve the fugitive additive in the solvent before mixing the fugitive additive with the inorganic material (as in Examples 1 and 3–9).

The invention is further illustrated by reference to results of experiments and examples of separations that have been effected using the materials of the present invention.

Commercially available single purified macromolecules have been sorbed and eluted. These include serum albumin, γ-globulin, haemoglobin, lyzozyme, ribonuclease, phosphoglycerate kinase, lactate dehydrogenase, cytochrome c, urease, ovalbumin, myoglobin, thymus DNA, yeast RNA. Mixtures of purified proteins (e.g. ovalbumin, cytochrome c and γ-globulin), muscle extracts, and blood serum, have been chromatographed. The three proteins, bovine serum albumin, γ-globulin and cytochrome c, have been separated individually from a synthetic mixture thereof. Separations have been carried out at temperatures between 2°C and room temperature (say 25°C), and at atmospheric pressures. The materials have been used in glass columns with bed dimensions up to 1 cm diameter and 50 cm length, but larger columns may be used for larger scale operations.

Flow rates up to 500 ml/hr have been used with 1 × 50 cm columns (660 ml/cm$^2$/hr or 10 bed volumes/hr) and separations have been carried out at pH's between 3 and 10. The optimum pH of sorption depends on the surface properties of the protein, its stability at the pH values being used and the nature of the particular sorbent material. Sorption on oxides may take place over a wide range of pH values since sorbent material and protein are amphoteric, but this may not be as marked with insoluble salts.

In most cases the macromolecules were dissolved in solutions containing buffers to maintain the optimum pH; EDTA may be incorporated to stabilise enzymes in the case of some sorbent oxides. It should be noted that in the case of oxides particularly, sorption is not inhibited by salts such as NaCl (M) nor by $(NH_4)_2SO_4$ (0.3M). Rapid sorption from dilute (0.1 mg/ml) solution has been observed using columns of sorbent. Thus, since macromolecule-containing substances often contain salts such as sodium chloride and ammonium sulphate from previous separation steps, inorganic materials have advantages over organic ion exchange materials since the former material will operate without the need to remove these salts whereas the latter material often will not.

Calcium phosphate has been regenerated by elution with 400 mM phosphate solution and 0.1N NaOH solution, as has barium sulphate. Oxides have been regenerated with 400 mM phosphate, 100 mM pyrophosphate and 0.1N sodium hydroxide. Unlike organic materials, thorough cleaning of inorganic materials, when necessary, can be achieved by reheating at elevated temperatures 100°–1400°C depending on the material, generally in air at atmospheric pressure.

It has been found that macromolecules may be eluted from calcium phsophate and barium sulphate with phosphate buffers of varying ionic strengths. For oxides, citrate, phosphate and pyrophosphate have been used either as gradients or as discrete steps.

Chromatograms of bovine serum albumin have been obtained using calcium phosphate particles, and it was found possible to exclude bovine serum albumin from sorption by use of particles having small pores.

Of the proteins tested little or no elution from titania was achieved with sodium chloride concentrations as high as 1M, however proteins were eluted with citrate, phosphate and pyrophosphate solutions.

In the situation where the molecules sorbed by the particles are present as an impurity in a substance (e.g. antigenic proteins in a vaccine), the sorbed molecules need not be eluted by use of an eluting agent, because since the impurity constitutes an unwanted product the particles may to heated to burn out the impurity molecules and leave the particles ready for re-use. Alternatively the sorbed molecules can be removed with strong acid or alkali, depending on the material of the particles. It is to be understood that the particles are substantially resistant to micro-biological attack and therefore the "useful life" of the particles is not limited by contact with microorganisms.

Some examples of separations according to the present invention are given below.

EXAMPLE 10

This example demonstrates the separation of macromolecules.

Open pore titanium dioxide particles were suspended in 5 mM phosphate buffer at pH 8.0, the particles were washed several times with the same buffer and fines were decanted. They were then poured into a 1 × 50 cm glass column fitted with a frit. The above buffer was pumped through the column, which was then subjected to a whole elution and regeneration cycle before loading with macromolecular material. A sample of macromolecules dissolved in the above buffer was loaded onto the column and the column was then treated with a series of buffers automatically distributed by means of a programmed multichannel valve apparatus. (Described in the specification of British Pat. No. 1,172,356). The eluate was monitored by U.V. absorption with a flow through detector and was collected in a fraction collector.

An ammonium sulphate fraction from horse muscle was fractionated to give a number of discrete protein-containing peaks. The peaks containing phosphoglycerate kinase were plotted and it was found that approximately 70% of the enzymic activity had been recovered.

EXAMPLE 11

This example demonstrates the concentration of a protein from dilute solution.

A column was prepared as in Example 10. A solution containing proteins in dilute solution (e.g. 0.1 mg/ml and pH∼8, 0.01M ammonium acetate) was pumped through the column (e.g. 1 × 50 cm) at 600 ml/cm$^2$/hr, the eluate being monitored continuously as in Example 10. When protein appeared in the eluate, the feed was stopped, 0.1M sodium pyrophosphate was pumped through the column and UV absorbing material was collected and pooled and assayed for phosphoglycerate kinase activity. Concentration factors of up to 40 were achieved. Good sorption of enzymic activity was achieved at this high flow-rate together with acceptable recovery of enzymic acitivity (∼70%). It was found that the sorbed molecules could be fractionated as in Example 10. Separation and fractionation results similar to those described in Examples 10 and 11 have been obtained with several oxides.

In elution experiments similar elution curves have been obtained with commercially available hydroxylapatite and the material of the present invention. It has also been found that reproducible chromatograms can be obtained over an extended period of time by successive regeneration of the column material in situ. For example, hydroxylapatite may be used in the separations of bovine serum albumin by using eluents of different phosphate concentrations in an automatic system. In this instance the hydroxylapatite may be regenerated by washing with alkali to remove the sorbed protein, and re-equilibration can be readily achieved using a low molarity phosphate.

$TiO_2$ and $Al_2O_3$ appear to be "complementary" with regard to macromaleable separations.

Thus, proteins such as albumin, for example are not sorbed readily in $TiO_2$ but are sorbed more readily on $Al_2O_3$. The converse situation is true for $\gamma$-globulin for example.

The foregoing description relates to particles composed of a single material, however, it is believed that particles, which can be used for the selective retention of molecules, can be formed by surrounding a sorptive core or kernel with a porous material, said porous material being arranged to act in the manner of a molecular sieve.

The following list gives examples of applications of the present invention:
a. Fractionation of proteins, including enzymes and antigens.
b. Fractionation of nucleotides and polynucleotides.
c. Separation of proteins from polynucleotides.
d. Separation of macromolecules from small molecules (e.g. antigenic protein from antibiotics).
e. Concentration of macromolecules from dilute solution (e.g. from culture filtrates of bacteria; from effluents such as milk whey).
f. Vaccine purification (antigenic proteins from virus preparations).
g. Purification and separation of carbohydrates.
h. As solid supports for enzymes and immunoadsorbents. For example, a bed of biologically active material can be prepared by sorbing an enzyme onto particles contained in a column. The enzyme remains substantially active in the bed in a number of cases and can be removed after use by washing with pyrophosphate, alkali or by heating, thus regenerating the bed for use.

It will be appreciated that if a molecule will not interact with the materials of the present invention to be sorbed (e.g. if the molecule has similar surface charges to the material at the pH used, or the molecule is uncharged) then separation may still occur by a "molecular sieve" action on the materials.

It will further be appreciated that whilst the foregoing examples are concerned predominantly with the separation of macromolecules, the materials according to the present invention may be used for the separation of other molecules which can be sorbed thereon.

We claim:

1. A method for producing an inorganic material having interconnected porosity throughout the material for the selective retention of predetermined molecules from a fluid substance containing said molecules including the steps of: mixing a finely divided, substantially insoluble, sorptive, inorganic material, capable of sorbing the molecules, with a solid fugitive additive to form a mixture, including in the mixture a solvent to dissolve fugitive additive in the solvent, said inorganic material being substantially insoluble in said solvent, forming discrete particles from the mixture, and heating the particles to remove solvent and fugitive additive to produce discrete particles of said inorganic material having an interconnected pore structure throughout said discrete particles providing an extended surface area, the pore size being such as will allow said predetermined molecules in said fluid substance to permeate the inorganic particles and be sorbed, said inorganic material being substantially unaffected by said heating utilized to effect removal of solvent and fugitive additive.

2. A method for producing a material for the selective retention of predetermined molecules from a fluid substance containing said molecules according to claim 1, wherein a binding agent is included in the mixture.

3. A method according to claim 1, wherein the fugitive additive is selected from the group consisting of ammonium carbonate, haemoglobin, dextran, polyvinyl alcohol, urea, bovine serum albumin and ovalbumin.

4. A method according to claim 2, wherein the fugitive additive is selected from the group consisting of ammonium carbonate, haemoglobin, dextran, polyvinyl alcohol, urea, bovine serum albumin and ovalbumin.

5. A method according to claim 1, wherein the finely divided, substantially insoluble, sorptive, inorganic material is selected from the group consisting of titanium dioxide, aluminum oxide, barium sulphate, calcium phosphate, zirconium oxide and calcium sulphate.

6. A method according to claim 2, wherein the finely divided, substantially insoluble, sorptive, inorganic material is selected from the group consisting of titanium dioxide, aluminium oxide, barium sulphate, calcium phosphate, zirconium oxide and calcium sulphate.

7. A method according to claim 1, wherein the finely divided, substantially insoluble, sorptive, inorganic material is a natural earth.

8. A method according to claim 2, wherein the finely divided, substantially insoluble, sorptive, inorganic material is a natural earth.

9. A method according to claim 1, wherein the particles produced are substantially spherical in shape.

10. A method according to claim 1, wherein the particles produced have a size in the range 50–600 $\mu$ diameter.

11. An inorganic material having interconnected porosity throughout the material for the selective retention of predetermined molecules from a fluid substance, said inorganic material being made by the process of claim 1.

* * * * *